United States Patent
Vancompernolle (10) Patent No.: US 7,198,931 B2
(45) Date of Patent: Apr. 3, 2007

(54) PHOSPHORYLATED GLYOXALASE I AND ITS USE

(75) Inventor: Katia Vancompernolle, Heusden (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 237 days.

(21) Appl. No.: 10/630,451

(22) Filed: Jul. 30, 2003

(65) Prior Publication Data

US 2004/0067567 A1 Apr. 8, 2004

Related U.S. Application Data

(63) Continuation of application No. PCT/EP02/01118, filed on Jan. 30, 2002.

(30) Foreign Application Priority Data

Jan. 31, 2001 (EP) .................... 01200353

(51) Int. Cl.
- C12N 9/88 (2006.01)
- C12N 9/00 (2006.01)
- A61K 38/00 (2006.01)
- A61K 38/16 (2006.01)
- C07K 1/00 (2006.01)

(52) U.S. Cl. .................... 435/232; 424/94.1; 424/94.5; 435/183; 530/350; 530/352

(58) Field of Classification Search ............... 424/94.1, 424/94.5; 435/183, 232; 530/350, 352
See application file for complete search history.

(56) References Cited

FOREIGN PATENT DOCUMENTS

WO WO 02/061065 8/2002

OTHER PUBLICATIONS

Ranganathan et al. Accession A46714. Mar. 3, 1994.*
Pestka et al. Protein Expr Purif. Nov. 1999;17(2):203-14.*
Patent Abstracts of Japan, 1993, 1 page.
Guy et al., Interleukin I and Tumor Necrosis Factor Activate Common Multiple Protein Kinases in Human Fibroblasts, The Journal of Biological Chemistry, 1991, pp. 14343-14352, vol. 266, No. 22.
Inoue et al., Secual Response of *Saccharomyces cerevisiae*: Phosphorylation of Yeast Glyoxalase I by a Cell Extract of Mating Factor-Treated Cells, J. Biochem, 1990, pp. 4-6, vol. 108.
Kim et al., Human Glyoxalase I, The Journal of Biological Chemistry, 1993, pp. 11217-11221, vol. 268, No. 15.
Ranganathan et al., The Journal of Biological Chemistry, 1993, pp. 5661-5667, vol. 268, No. 8.
Sakamoto et al., Glyoxalase I is involved in resistance of human leukemia cells to antitumor agent-induced apoptosis, Blood, May 15, 2000, pp. 3214-3218, vol. 95, No. 10.
Thornalley et al., Advances in glyoxalase research. Glyoxalase expression in malignancy, anti-proliferative effects of methylglyoxal, glyoxalase I inhibitor diesters and S-D-lactoylglutathione, and methylglyoxal-modified protein binding and endocytosis by the advanced glycation endproduct receptor, Critical Reviews in Oncology/Hematology, 1995, pp. 99-128, vol. 20.
Van Herreweghe et al., Tumor necrosis factor-induced modulation of glyoxalase I activities through phosphorylation by PKA results in cell death and is accompanied by the formation of a specific methylglyoxal-derived AGE, Proceedings of the National Academy of Sciences of the United States, Jan. 22, 2002, pp. 949-954, vol. 99, No. 2.
Inoue et al., "Sexual Response of *Saccharomyces cerevisiae*: Phosphorylation of Yeast Glyoxalase I by a Cell Extract of Mating Factor-Treated Cells," J. Biochem, 1990, pp. 4-6, vol. 108.
Oya et al., "Methylglyoxal Modification of Protein," The Journal of Biological Chemistry, Jun. 25, 1999, pp. 18492-18502, vol. 274, No. 26.
Sakamoto et al., "Modulation of Heat-shock Protein 27 (Hsp27) Anti-apoptotic Activity by Methylglyoxal Modification," The Journal of Biological Chemistry, Nov. 29, 2002, pp. 45770-45775, vol. 277, No. 48.

* cited by examiner

Primary Examiner—Tekchand Saidha
Assistant Examiner—Christian L. Fronda
(74) Attorney, Agent, or Firm—TraskBritt (57) ABSTRACT

The present invention relates to a phosphorylated form of mammalian glyoxalase I. The present invention relates further to the use of phosphorylated mammalian glyoxalase I to modulate MG-modification of proteins (AGE formation) and consequent cell death, especially upon stress such as oxidative stress, or upon TNF treatment.

2 Claims, 8 Drawing Sheets

IEF pH4-7

SEQUENCE LISTING

<160> NUMBER OF SEQ ID NOS: 3

<210> SEQ ID NO 1
<211> LENGTH: 184
<212> TYPE: PRT
<213> ORGANISM: Homo sapiens
<220> FEATURE:
<223> OTHER INFORMATION: Lactoylglutathione lyase; Glyoxalase I: Accession Q04760

<400> SEQUENCE: 1

```
Met Ala Glu Pro Gln Pro Pro Ser Gly Gly Leu Thr Asp Glu Ala Ala
 1               5                  10                  15

Leu Ser Cys Cys Ser Asp Ala Asp Pro Ser Thr Lys Asp Phe Leu Leu
            20                  25                  30

Gln Gln Thr Met Leu Arg Val Lys Asp Pro Lys Lys Ser Leu Asp Phe
        35                  40                  45

Tyr Thr Arg Val Leu Gly Met Thr Leu Ile Gln Lys Cys Asp Phe Pro
    50                  55                  60

Ile Met Lys Phe Ser Leu Tyr Phe Leu Ala Tyr Glu Asp Lys Asn Asp
65                  70                  75                  80

Ile Pro Lys Glu Lys Asp Glu Lys Ile Ala Trp Ala Leu Ser Arg Lys
                85                  90                  95

Ala Thr Leu Glu Leu Thr His Asn Trp Gly Thr Glu Asp Asp Ala Thr
            100                 105                 110

Gln Ser Tyr His Asn Gly Asn Ser Asp Pro Arg Gly Phe Gly His Ile
        115                 120                 125

Gly Ile Ala Val Pro Asp Val Tyr Ser Ala Cys Lys Arg Phe Glu Glu
    130                 135                 140

Leu Gly Val Lys Phe Val Lys Lys Pro Asp Asp Gly Lys Met Lys Gly
145                 150                 155                 160

Leu Ala Phe Ile Gln Asp Pro Asp Gly Tyr Trp Ile Glu Ile Leu Asn
                165                 170                 175

Pro Asn Lys Met Ala Thr Leu Met
            180
```

<210> SEQ ID NO 2
<211> LENGTH: 7
<212> TYPE: PRT
<213> ORGANISM: Homo sapiens

<400> SEQUENCE: 2

```
Ser Leu Asp Phe Tyr Thr Arg
 1               5
```

<210> SEQ ID NO 3
<211> LENGTH: 11
<212> TYPE: PRT
<213> ORGANISM: Homo sapiens

<400> SEQUENCE: 3

```
Phe Asp Leu Tyr Phe Leu Ala Tyr Glu Asp Lys
 1               5                  10
```

PHOSPHORYLATED GLYOXALASE I AND ITS USE

CROSS-REFERENCE TO RELATED APPLICATIONS

This application is a continuation of co-pending International Patent Application No. PCT/EP02/01118 filed on Jan. 30, 2002 designating the United States of America (International Publication No. WO 02/061065 published on Aug. 8, 2002), the contents of the entirety of which are incorporated by this reference, which claims priority to European Patent Application No. 01200353.9, filed Jan. 31, 2001, which is incorporated herein by reference in its entirety.

TECHNICAL FIELD

The present invention relates to a phosphorylated form of mammalian glyoxalase I. The present invention relates further to the use of phosphorylated mammalian glyoxalase I to modulate methylglyoxal (MG)-modification of proteins and consequent cell death, especially upon stress such as oxidative stress, or upon TNF treatment.

BACKGROUND

Tumor Necrosis Factor (TNF) is a pleiotropic cytokine, originally described for its ability to cause hemorrhagic necrosis of certain tumors in vivo (Carswell et al., 1975). In addition to its anti-tumor and anti-malignant cell effects, TNF has been reported to influence mitogenesis, differentiation and immunoregulation of various cell types.

The activities of TNF are mediated through two cell-surface receptors, namely TNF-R55 (CD120a) and TNF-R75 (CD120b), which are expressed by most cell types. TNF's effects are mediated primarily through TNF-R55. Upon activation of the receptor, adaptor proteins such as TRADD and TRAF are recruited and bind to the intracellular part of the clustered receptor (for review, see Wallach et al., 1999). These receptor-associated molecules that initiate signaling events are largely specific to the TNF/nerve growth factor receptor family. However, the downstream signaling molecules are not unique to the TNF system, but also mediate effects of other inducers. Downstream signaling molecules in the TNF system identified so far include: caspases, phospholipases, the three mitogen-activated protein (MAP) kinases, and the NF-κB activation cascade.

TNF-induced cell death in L929 cells is characterized by a necrosis-like phenotype and does not involve DNA fragmentation (reviewed by Fiers et al., 1999). It is independent of caspase activation and cytochrome c release, but is dependent on mitochondria and is accompanied by increased production of reactive oxygen intermediates (ROI) in the mitochondria that are essential to the death process (Goossens et al., 1995; Goossens et al., 1999). The latter was demonstrated by the fact that lipophylic anti-oxidantia, when added three hours after TNF treatment, could not only arrest the ongoing increased ROI production, but could also arrest cell death (Goossens et al., 1995). Furthermore, the mitochondria translocate from a dispersed distribution to a perinuclear cluster (De Vos et al., 2000); functional implications of this mitochondrial translocation remain unclear.

Glyoxalase I, together with glyoxalase II, constitutes the glyoxalase system that is an integral component of the cellular metabolism of α-ketoaldehydes and is responsible for the detoxification of the latter. The prime physiological substrate of the glyoxalase system is methylglyoxal (MG), which is cytotoxic. The major source of intracellular MG is the glycolysis namely, nonenzymatic and enzymatic elimination of phosphate from dihydroxyacetone phosphate and glyceraldehyde-3-phosphate. The glyoxalase system, using glutathione (GSH) as cofactor, catalyzes the conversion of methylglyoxal to D-lactate in two consecutive steps. Glyoxalase I catalyzes the isomerization of the hemithioacetal, produced by the nonenzymatic conjugation of methylglyoxal with glutathione (GSH), to S-D-lactoylglutathione which is then hydrolyzed by glyoxalase II to D-lactate and GSH. D-lactate is then further metabolized to pyruvate by 2-hydroxy-acid dehydrogenase localized in the mitochondria. In addition to its role as a detoxification system, it has been suggested that glyoxalase I, together with its substrate MG, is involved in the regulation of cellular growth (for a review, see Kalapos, 1999), but until now this role has not been found. Increased expression of glyoxalase I occurs in diabetic patients and in some types of tumors such as colon carcinoma (Ranganathan et al., 1993), breast cancer (Rulli et al., 2001), prostate cancer (Davidson et al., 1999). It is also uniquely overexpressed in invasive human ovarian cancer compared to the low malignant potential form of this cancer (Jones et al., 2002). Also, hypoxia can lead to increased expression of glyoxalase I (Principato et al., 1990). Recently, it has been shown that glyoxalase I is involved in resistance of human leukemia cells to anti-tumor agent-induced apoptosis (Sakamoto et al., 2000).

DISCLOSURE OF THE INVENTION

While much effort has been directed at the molecular mechanism of the caspase-dependent cell death pathway, relatively little is known about the TNF-induced ROI-dependent cell death pathway. To identify molecules involved in the latter, we performed a comparative study of the phosphoproteins from TNF-treated and control cells by two-dimensional (2-D) gel electrophoresis. It is known that upon activation of the TNF receptor, several kinases/phosphatases are activated (Guy et al., 1992; Guy et al., 1991). However, most of the changes in phosphorylation occur very rapidly (2 to 15 minutes) upon binding of TNF to its receptors and most of them are transient and related to the gene-inductive activities of TNF.

To identify molecules that are involved in the cytotoxic process downstream of the receptor-proximal events, lysates from cells that had been stimulated with TNF for 1.5 hours are studied. Previously, oncoprotein 18 (Op18, stathmin) has been identified as a protein with reproducible and large increases in phosphorylation upon TNF treatment. Op18 is responsible for TNF-induced microtubule stabilization that promotes cell death (Vancompenolle et al., 2000). Unexpectedly, we were able to demonstrate that glyoxalase I is also phosphorylated upon TNF treatment. Phosphorylation of mammalian glyoxalase I has not yet been described, although the sequence does contain several potential phosphorylation sites (Ranganathan et al., 1993). Interestingly, phosphorylation of yeast GLO1 has been observed during the sexual response of S. cerevisiae—specifically, during the arrest of cell division at the G1 phase, which occurs when haploid cells of one sex are exposed to the mating factor of the opposite type of cells (Inoue et al., 1990). However, none of these observations suggest that phosphorylated mammalian glyoxalase I does exist, neither which potential phosphorylation sites may be used.

It is a first aspect of the invention to provide phosphorylated mammalian glyoxalase. The phosphorylation may be a single or a multiple phosphorylation. A preferred embodiment is a phosphorylated mammalian glyoxalase I comprising SEQ ID NO:1. Preferentially, phosphorylated mammalian glyoxalase I essentially consists of SEQ ID NO:1. Even more preferentially, phosphorylated mammalian glyoxalase I consists of SEQ ID NO:1. Preferably, phosphorylation is carried out at position Ser 8 and/or Ser 21 and/or Ser 26 and/or Thr 107. Even more preferably, the phosphorylation is carried out at the PKA phosphorylation sites Ser 45 and/or Thr 98 (numbering as for human glyoxalase, including the N-terminal Met residue).

Another aspect of the invention is the use of a phosphorylated glyoxalase I to modulate MG-modification of proteins. Phosphorylated glyoxalase I may be any glyoxalase I, known to the person skilled in the art, such as a fungal glyoxalase I or a plant glyoxalase I. Preferably, glyoxalase I is a mammalian glyoxalase I. MG-modified proteins or advanced glycation end products (AGEs) are known to be synthesized in response upon a number of pathophysiological conditions in vivo, such as cataract formation (Shamsi 2000), vascular complications associated with chronic diabetes (Shinohara et al., 1998), tissue damage after ischemia/reperfusion (Oya et al., 1999) and aging (Corman et al., 1998). The term "AGE," as used here, is used for any MG-modification of a protein, irrespective of the way it is formed. The term "MG-modification of proteins" is considered as being equivalent with the term AGE formation.

Still another aspect of the invention is the use of phosphorylated glyoxalase I, or an inhibitor of the phosphorylation of glyoxalase I, preferably mammalian glyoxalase I to modulated TNF-induced cell death. This inhibitor can be any inhibitor that inhibits the phosphorylation of glyoxalse I. Preferably, the inhibitor is an inhibitor of the PKA activity.

Alternatively, a mutant form of glyoxalase I may be used that affects phosphorylation in it ("phosphorylation mutant"), i.e. it can no longer be phosphorylated at one or more phosphorylation sites and/or it becomes phosphorylated at other sites. On the basis of the knowledge of the phosphorylation sites, such mutants can be easily constructed by the person skilled in the art and include, as a nonlimiting example, glyoxalase I forms where the Ser 45 and/or the Thr 98 have been replaced by another amino acid or any other mutant that affects phosphorylation on these or other sites. Therefore, another aspect of the invention is the use of a phosphorylation mutant of glyoxalase I, preferably mammalian glyoxalase I, to modulate TNF-induced cell death. This modulation can be realized by replacing the endogenous glyoxalase I by the mutant form, or by expressing the mutant glyoxalase I form beside the endogenous glyoxalase I.

A further aspect of the invention is the use of phosphorylated glyoxalase I, or an inhibitor of the phosphorylation of glyoxalase I, or a phosphorylation mutant of glyoxalase I, to modulate stress-induced cell death. Preferably, the stress is oxidative stress. Oxidative stress, followed by ROI induction and AGE formation is known to occur in several organisms, including plants, yeast, fungi and mammalians. A preferred embodiment is the use of mammalian phosphorylated glyoxalase I to modulate oxidative stress-induced cell death.

Still another aspect of the invention is the use of PKA to phosphorylate glyoxalase I. By modulating the phosphorylation of glyoxalase I, TNF-induced cell death and stress-induced cell death, preferably oxidative stress, can be modulated.

BRIEF DESCRIPTION OF THE FIGURES

FIG. 8A: Western blot with the anti-AGE antibody mAb6B that was developed against MG-modified keyhole limpet hemocyanin (recognizes also MG-modified BSA). Immunocomplexes were visualized by enhanced chemiluminescence (ECL) and evaluated by scanning densitometry. To analyze AGE formation in TNF-induced cell death, all TNF treatments (1000 U/ml, 2.5 hours) were done in the presence of cycloheximide (CHX) to synchronize cell death. Equal amounts of total cytosolic protein from cells incubated under different conditions were loaded in each lane. a: control cells; b: TNF-treated cells; C: control anti-oxidant butylated hydroxyanisole (BHA; 100 µM); d: TNF-treated cells in the presence of BHA (100 µM), the antioxidant agent BHA was administered 0.5 hour after TNF administration to allow initiation of TNF signaling; e: control 2-deoxyglucose; f: TNF-treated cells in the presence of 2-deoxyglucose (2:1 ratio to glucose), 2-deoxyglucose was administered at the same time as TNF. Note the appearance of the specific MG-derived AGE exclusively in TNF-treated cells (indicated by arrowheads), while no significant changes in the other AGEs can be observed. The formation of this MG-derived AGE is strongly inhibited (65%) in the presence of BHA or 2-deoxyglucose.

DETAILED DESCRIPTION OF THE INVENTION

EXAMPLES

Materials and Methods to the Examples

Cell Lines and Cultures

All L929 cells were cultured in Dulbecco's modified Eagle's medium supplemented with heat-inactivated fetal calf serum (5% v/v), heat-inactivated newborn calf serum (5% v/v), penicillin (100 units/ml), streptomycin (0.1 mg/ml), and L-glutamine (2 mM), at 37° C. in a humidified incubator under a 5% $CO_2$ atmosphere.

Reagents

Murine TNF (mTNF) was obtained from Roche Diagnostics and was used at 1000 IU/ml unless indicated otherwise. Propidium iodide (PI) and cycloheximide (CHX) (all from Sigma) were used at concentrations of 30 μM and 50 μg/ml, respectively.

Measurement of TNF-induced Cell Death by Flow Cytometry

Cell death in L929 was induced by addition of TNF to the cell suspension. Cell death was measured by quantifying PI-positive cells by FACS (FACSCalibur, Becton Dickinson, San Jose, Calif.). The PI dye was excited with an argon-ion laser at 488 nm; PI fluorescence was measured above 590 nm using a long-pass filter. Routinely, 3,000 cells were analyzed. Cell death is expressed as the percentage of PI-positive cells in the total cell population.

Radiolabeling of Cells and Preparation of the Sub-Cellular Protein Fractions

L929 cells were plated 48 hours prior to the experiment. $^{32}P$ labeling was carried out as described in (Guy et al., 1992). TNF treatments (1000 IU/ml, 1.5 hours) were done in the presence of cycloheximide (CHX), to synchronize cell death. To simplify the 2-D phosphoprotein pattern and subsequent computer-assisted analysis, we prepared two subcellular protein fractions. The cytosolic protein fraction, containing soluble cytoplasmic molecules and molecules derived from single-membrane organelles, was obtained as the supernatant from digitonin (0.03%)-permeabilized cells. After rinsing once with excess PBS buffer, the remaining cell fraction was lysed in a CHAPS (2%)-containing buffer as described in (Guy et al., 1992). This lysate was then centrifuged (20,000 g) and the supernatant was used as the organelle fraction; it is enriched for mitochondrial and cytoskeleton-derived proteins.

Two-dimensional (2D) Gel Electrophoresis

Isoelectric focusing. Isoelectric focusing was carried out on 18 cm IPG strips, pH 4–7 (Amersham Pharmacia Biotech), according to the manufacturer's instructions. Protein samples were precipitated with ethanol and redissolved in lysis buffer.

SDS-PAGE. The second dimension (SDS-PAGE) was run on large vertical gels (12.5% acrylamide, Biorad).

Western Blotting

Proteins were separated by SDS-PAGE (12.5%) and transferred to a PVDF membrane (Hybond-P, Amersham Pharmacia Biotech). The blots were incubated with an anti-human glyoxalase I antibody (kindly provided by Dr. P. Thornalley, University of Essex, UK), followed by ECL-based detection (reagents of Amersham Pharmacia Biotech; software for analysis by Totallab).

Amino Acid Sequence Analysis by MALDI-mass Spectrometry

Following in-gel digestion of the excised protein with endoproteinase Lys-C (sequencing grade; Boehringer, Mannheim, Germany), a 10% aliquot of the generated peptide mixture was purified and concentrated on Poros® 50 R2 beads (Gevaert et al., 1998; Gevaert et al., 1997) and used for MALDI-MS peptide mass fingerprint analysis. However, partly due to contamination with human keratin peptides, the obtained peptide mass map did not lead to any unambiguous protein identification in a nonredundant protein database. Therefore, the remainder of the peptide mixture was separated by RP-HPLC, a total of 20 fractions containing eluting peptides were obtained, which were all analyzed by MALDI-MS. Adequate peptide ions were further selected for post-source decay (PSD) analysis (Spengler et al., 1992). A PSD-spectrum obtained from a peptide ion with a mass of 902.42 Da (measured in linear mode) present in the first RP-HPLC fraction, could be unambiguously assigned to the peptide $NH_2$-SLDFYTR-COOH (SEQ ID NO: 2) present in human glyoxalase I (database entry number 417246) using the SEQUEST algorithm and a nonredundant protein database. Following a search in an EST-database, the same peptide sequence was identified in many different mouse EST-clones. The identified peptide contains an arginine residue at its C-terminus instead of a lysine, an observation which we made several times when endoproteinase Lys-C was used as the protease.

In order to confirm our initial finding, PSD-analysis was conducted on a peptide with an apparent mass of 1396.53 Da present in RP-HPLC fraction 11. Based on the partially $^{18}O$-labeled y-type fragment ions, a peptide sequence tag (391.24)YAI/LF(885.67) could easily be obtained. Furthermore, a SEQUEST search in a nonredundant protein database lead to the identification of the peptide $NH_2$-FSLY-FLAYEDK-COOH (SEQ ID NO: 3) also belonging to human glyoxalase I. Again, the same peptide sequence was found in different mouse EST clones using the PSD data and a SEQUEST search in an EST database. Based upon the amino acid sequence of human glyoxalase I, masses of peptide ions observed in the different RP-HPLC fractions could be assigned to the identified protein. Hereby, a total of 38% of the amino acid sequence of the protein was covered, again confirming the identification of glyoxalase I.

Assay of Glyoxalase I Activity

The glyoxalase I assay was performed according to a spectrophotometric method monitoring the increase in absorbance at 240 nm due to the formation of S-D-lactoyl-glutathione for 4 minutes at 20° C. The standard assay mixture contained 2 mM MG and 2 mM GSH in a sodium phosphate buffer (50 mM, pH 6.6). Before initiating the reaction by adding the total cytosolic protein fraction to the assay mixture, the mixture was allowed to stand for 10 minutes to ensure the equilibration of hemithioacetal formation.

D-Lactate Measurements

D-Lactate measurements were performed by a fluorimetric assay using an endpoint enzymatic assay with D-lactate dehydrogenase (McLellan et al. 1992).

Intracellular Methylglyoxal Measurements

Intracellular free methylglyoxal is detected as the 2-methylquinoxaline (2-MQ) derivative of methylglyoxal formed with o-phenylenediamine (o-PD) using the general approach of (Chaplen et al., 1996). Samples arrived frozen on dry ice and were stored at 20° C. until assayed. Samples were thawed at room temperature and maintained on ice during the assay procedure. Sample volume was increased to 2.5 ml with MilliQ water and the samples were sonicated (5 s, 30 W). 5 M HClO4 (PCA; 0.25 ml) was added to precipitate macromolecules and the resulting mixture was incubated on ice for 20 minutes. Samples were then centrifuged (12,000xg, 10 minutes) to remove precipitated materials. The supernatant was passed through a C-18 SPE cartridge (Waters Sep-Pak tC18 plus cartridge, Millipore Corp., Marlborough, Mass.) that had been prepared by flushing with 6–8 ml of acetonitrile followed by 6–8 ml of 10 mM KH2PO4 (pH 2.5, adjusted with concentrated H3PO4). The prederivatization SPE step removes phenol red and other interfering compounds. Samples were supplemented with 12.5 nmol 5-methylquinoxaline (5-MQ; internal standard) and 250 nmol o-PD (derivatizing agent) and reacted at 20° C. for 3.5 to 4 hours.

Sample Concentration

All samples are concentrated after derivatization. For concentration, the samples are passed through a C-18 SPE cartridge, prepared as described above, at a rate of 1–2 ml/minutes. The cartridges are then rinsed with 1–2 ml 10 mM KH2PO4 (pH 2.5) and the retentate eluted with 2 ml of acetonitrile. Eluates were evaporated to a volume of 200 ml using a Savant Speed-Vac Concentrator vacuum centrifugation unit (Savant Instruments, Farmingdale, NY) and filtered through 0.2 mm Gelman PVDF filters (Fisher Scientific, Chicago, Ill.) into sample vials.

HPLC of Quinoxalines

HPLC was performed as described previously (Chaplen et al., 1996) but with a mobile phase consisting of 35% acetonitrile/0.1% trifluoroacetic acid, pH 2.4 and 65% 10 mM phosphate/0.1% trifluoroacetic acetic acid in HPLC grade water, pH 2.4. Under these modified conditions, 2-MQ eluted after 7.5 minutes and 5-MQ eluted after 11.2 minutes.

Detection of MG-derived AGEs

L929 cells were seeded 48 hours prior to the experiment. TNF incubations (1000 U/ml) were done in the presence of CHX to synchronize cell death. After TNF incubations (1.5 hours or 2.5 hours), the cells were rinsed three times with ice-cold PBS buffer and cell lysates were prepared in a CHAPS-containing cytosol extraction buffer (Guy et al., 1992). MG-derived AGEs were detected by Western blotting using the mAb6B (Oya et al., 1999). To use the antibody sparingly, SDS-PAGE gels were only run over a distance of 5 cm.

Example 1

TNF Induces Increased Phosphorylation of Glyoxalase I

Figure 1:
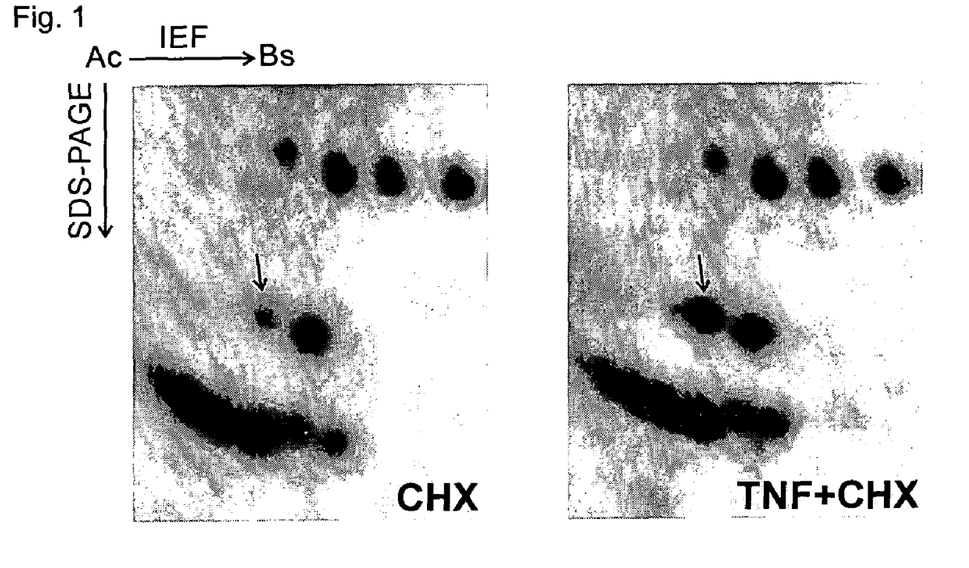
FIG. 1: phosphorylation of glyoxalase I in control cells (left panel) and after 1.5 hours of TNF treatment (right panel).

FIG. 1 shows the autoradiogram of the two-dimensional gels from TNF-treated and control samples that were derived from cells labeled with $^{32}$P-orthophosphate. The protein spot with increased phosphorylation identified as glyoxalase I is indicated by an arrow. It was identified by mass spectrometry analysis of a peptide mixture derived from an in-gel digestion of the excised protein spot. The increased phosphorylation of glyoxalase I is already observed after 15 minutes of TNF treatment, but is much more pronounced after 1.5 hours of TNF treatment (FIG. 1). This indicates that the TNF-induced phosphorylation of GLO1 is an early but lasting event.

Example 2

Figure 2:
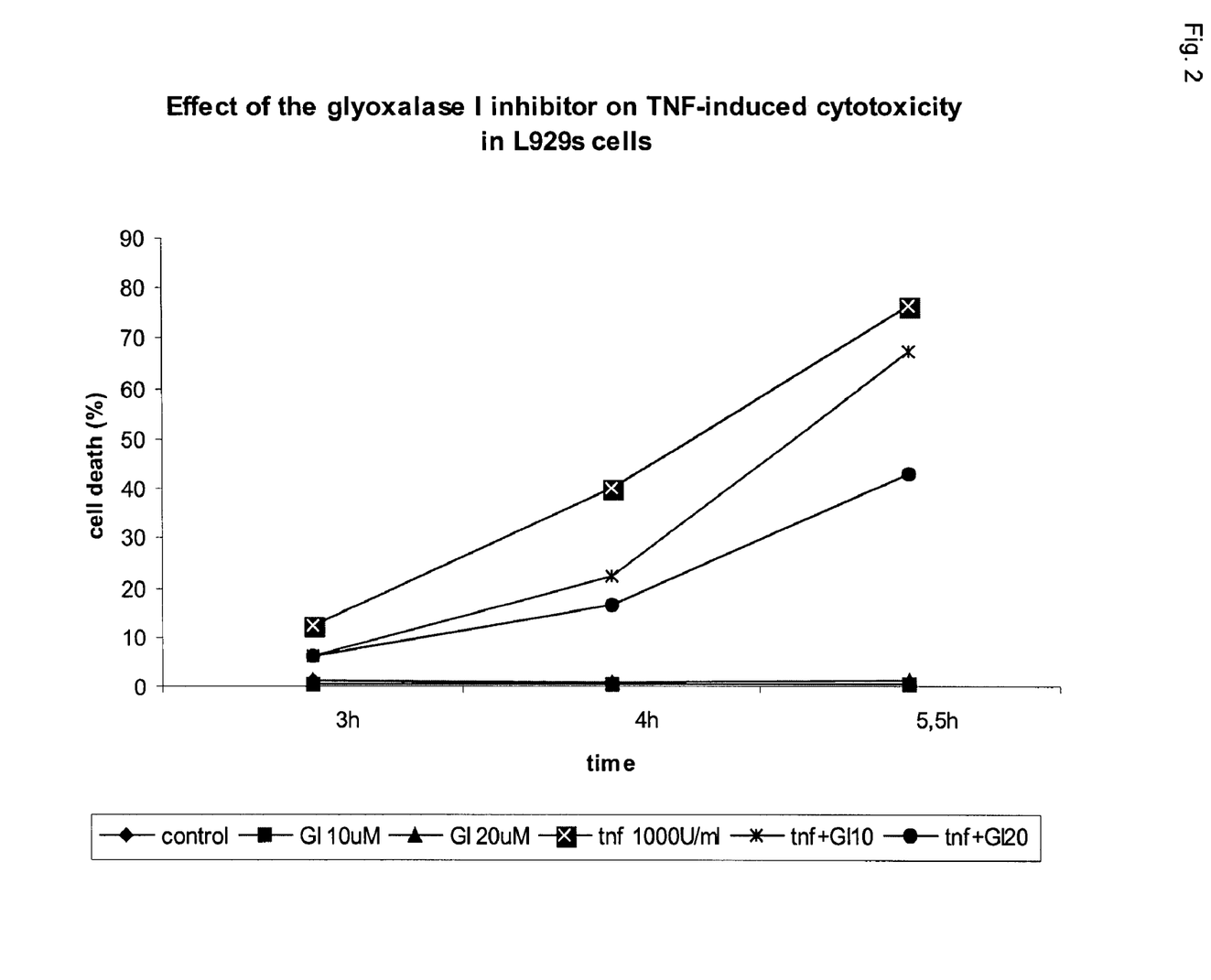
FIG. 2: effect of the glyoxalase I inibitor S-p-bromobenzylglutathione diester on TNF-induced cytotoxicity in L929s cells, in function of the incubation time. TNF is added at a concentration of 1000 units/ml; the inhibitor is added 1 hour 10 minutes prior to TNF at a concentration of 10 µM (GI10) or 20 µM (GI20). The time scale is calculated from the moment of TNF addition.

The Glyoxalase I Inhibitor
S-p-bromobenzylglutathione Cyclopentyl Diester
Inhibits TNF-induced Cell Death To examine the role of glyoxalase I in TNF-induced cell death, we tested the effect of the cell permeable competitive inhibitor of glyoxalase I S-p-bromobenzylglutathione diester on cell death. Preincubation (1 hour 10 minutes) of L929 cells with this inhibitor strongly inhibits TNF-induced cell death in a concentration-dependent manner (FIG. 2). An inhibition of 60% was obtained at a concentration of 20 μM of the inhibitor. However, when the inhibitor and TNF were added at the same time, a synergistic effect on TNF-induced cell death was obtained (50% increase in cell death at a concentration of 20 μM of the inhibitor). This synergistic effect is more pronounced at lower doses of TNF; that is, when the cells die more slowly.

Example 3

Figure 3:
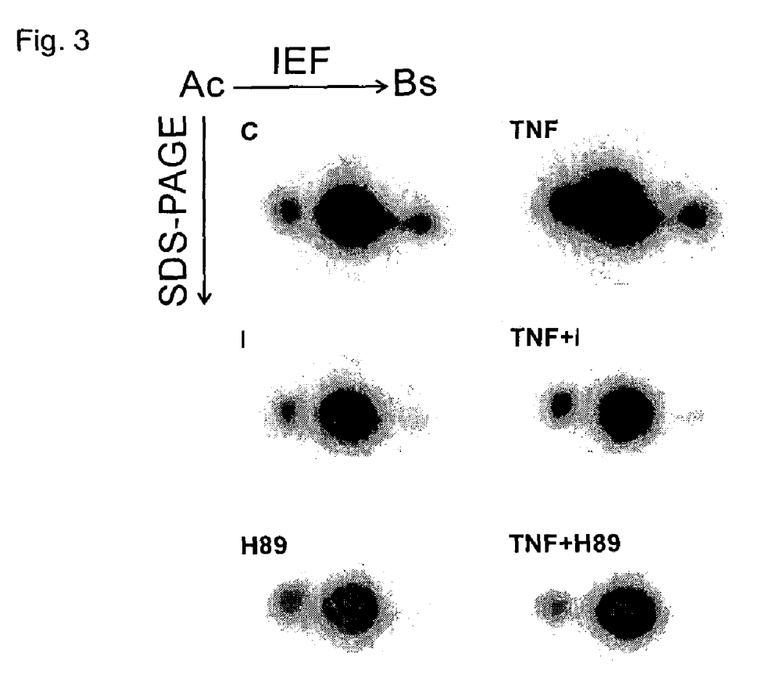
FIG. 3: western blots, developed with anti-human glyoxalase I polyclonal antibody, of 2-dimensional gels (pH 3–10) from total cell lysates derived from control cells (C), glyoxalase I inhibitor S-p-bromobenzylglutathione diester treated cells (I), TNF-treated cells (TNF) and cells treated with TNF and glyoxalase I inhibitor (TNF+I).

The Glyoxalase I Inhibitor
S-p-bromobenzylglutathione Cyclopentyl Diester
Inhibits the TNF-induced Phosorylation of
Glyoxalase I This differential effect of the inhibitor on TNF-induced cell death prompted us to investigate whether the binding of the inhibitor to GLO1 competes and thus inhibits the TNF-induced phosphorylation of GLO1. FIG. 3 shows the Western blots, developed with an anti-human glyoxalase I polyclonal antibody, of 2-dimensional gels (pH 3–10) from total cell lysates derived from TNF-treated and control cells and from TNF-treated and control cells that were first preincubated with the glyoxalase I inhibitor for 1 hour 10 minutes. In the upper panels, you can see that TNF induces a more acidic phosphoisoform of glyoxalase I which is not well separated from the nonphosphorylated form (fills the space between the most left isoform and the main nonphosphorylated form. In the lower panels, you can see that in the presence of the glyoxalase I inhibitor, TNF cannot induce the more acidic phosphoisoform of glyoxalase I (identical 2-D patterns as in the control). These data show that the competitive inhibitor of glyoxalase I S-p-bromobenzylglutathione inhibits the TNF-induced phosphorylation of GLO1 and that phosphorylated glyoxalase I is essential for cell death. These data also suggest that phosphorylation of glyoxalase I modulates the active site of the enzyme.

Thus, the differential effect of the GLO1 inhibitor on TNF-induced cell death can be explained as follows:

when the cells are pretreated with the inhibitor, the inhibitor is already bound to GLO1 and thus hinders the TNF-induced phosphorylation of GLO1 which then leads to inhibition of phosphorylated GLO1-mediated MG-modification of proteins and consequent cell death.

however, when the cells are treated with the inhibitor and TNF together, the TNF-induced phosphorylation of GLO1 occurs first (via a receptor-activated kinase cascade) and the inhibitor can only bind to nonphosphorylated GLO1 (and not to phosphorylated GLO1) leading to inhibition of GLO1 and thus to accumulation of MG, resulting in phosphorylated GLO1-mediated MG-modification of proteins and consequent cell death.

Example 4

TNF-induced Phosphorylation of Glyoxalse I does not Inhibit Methylglyoxal Detoxification For many years, α-ketoaldehydes, exemplified by methylglyoxal, have been known to be carcinostatic, but their direct use as anti-cancer drugs is prevented by their rapid detoxification in vivo by the glyoxalase system. Therefore, glyoxalase I inhibitors have been developed as potential anti-cancer agents (Vince and Wadd, 1969; Thornalley et al., 1996). Bearing this in mind, one would expect that TNF-induced phosphorylation of GLO1 would result in inhibition of the enzyme and thus in accumulation of MG with cytotoxicity as a consequence. However, our experiments with the GLO1 inhibitor do not support this expectation, because we would then expect a synergistic effect of the preincubated inhibitor on TNF-induced cell death. Indeed, measurements of GLO1 activity in lysates derived from TNF-treated and control cells showed no inhibition, but even a limited increase in GLO1 activity in TNF-treated cells. These experiments were repeated several times and each time gave the same results, with an average increase of 8% after 1 hour of TNF treatment and 12% (from 0.086±0.003 to 0.106±0.001 units per 8.5 µg of total protein) after 1.5 hours of TNF treatment. Measurement of the concentration of the end product of the glyoxalase system D-lactate showed an increase of 60% after 1.5 hours of TNF treatment compared to control cells. This further confirmed that TNF did not inhibit GLO1 activity and that an increased flux of MG is converted through the glyoxalase system in TNF-treated cells.

Example 5

TNF Increases the Intracellular Concentrations of Methylglyoxal

As we consider it very unlikely that TNF would cause an increased detoxification of MG through the glyoxalase system, a more plausible explanation is that TNF induces an increase in the intracellular concentrations of MG via a pathway other than inhibition of glyoxalase I. An increase in the intracellular concentration of MG would then also automatically result in an increased flux of MG through the glyoxalase system and an increased GLO1 activity. Therefore, intracellular concentrations of MG were measured with a method that not only measures free MG, but also MG bound to biological molecules (majority of the MG), mainly proteins (Chaplen et al., 1998). Two independent experiments were performed in which intracellular concentrations of MG were measured in TNF-treated (1.5 hours) L929 cells compared to control cells. Each sample was measured in triplicate and each time gave very reproducible results. These results showed that TNF strongly increased the intracellular concentrations of MG, with an increase of 32% (from 0.91 µMole in control cells to 1.20 µMole in TNF-treated cells) in the one experiment and 94% (from 1,24 µMole in control cells to 2.39 µMole in TNF-treated cells) in the other experiment.

Figure 4:
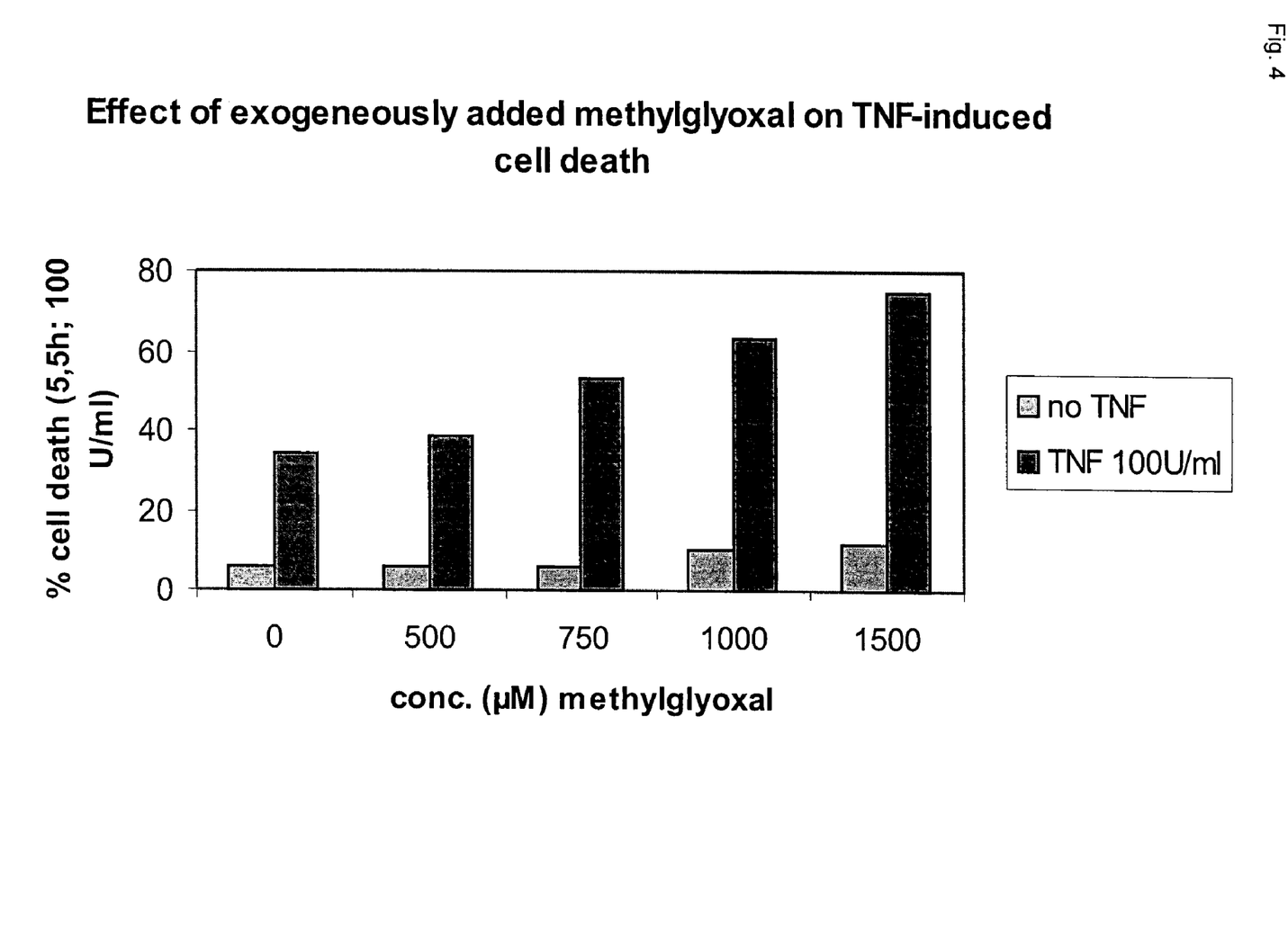
FIG. 4: effect of different concentrations exogeneously added methylglyoxal on TNF-induced cell death. Measurement after 5.5 hours of incubation with TNF and methylglyoxal at a concentration as indicated.

Also, exogeneously added MG is strongly synergistic with TNF-induced cell death in a concentration-dependent manner (FIG. 4), while MG alone and used at the same concentrations is not cytotoxic for L929 cells. The synergistic effect of exogeneously added MG is more pronounced at lower doses of TNF (100 U/ml) and also earlier in TNF treatment. This result can be explained by the fact that the TNF-induced increase of endogenous MG is more drastic at higher doses of TNF (1000 U/ml) and later in TNF treatment.

Example 6

Inhibition of AGE Formation Inhibits TNF-induced Cell Death

Figure 5:
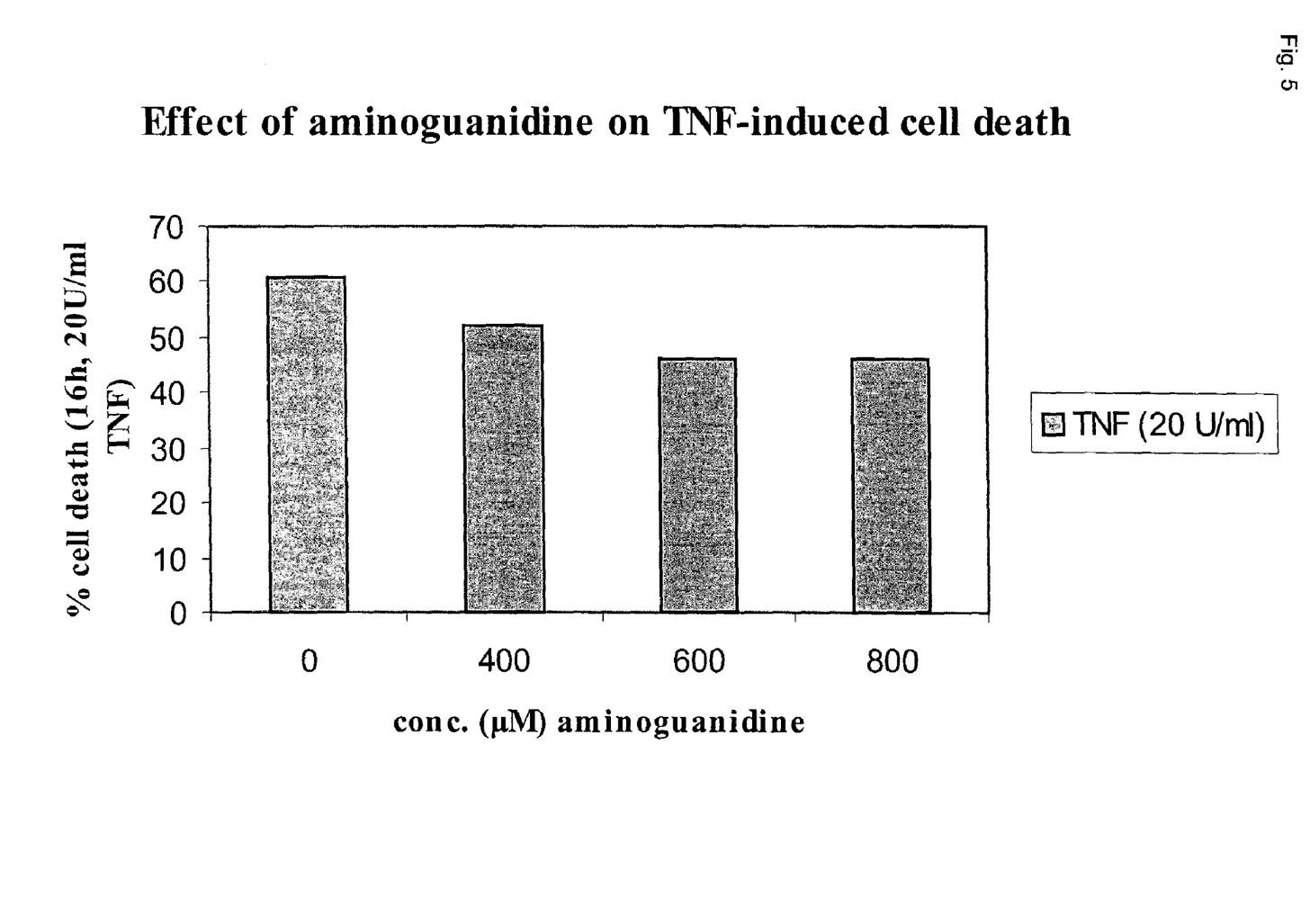
FIG. 5: effect of different concentrations of the AGE formation inhibitor, aminoguanidine, on the TNF-induced cell death. Measurement after 16 hours of incubation with TNF and aminoguanidine at a concentration as indicated.

Increased endogenously produced levels of dicarbonyls, especially methylglyoxal, are involved in numerous pathogenic processes in vivo, including the formation of advanced glycation end-products (AGEs) which contribute to the pathophysiology of aging and to complications associated with chronic diabetes. They have been detected in several pathophysiological conditions in vivo, such as cataract formation, vascular complications in diabetes, and tissue damage after ischemia/reperfusion. All these conditions are characterized by increased oxidative stress, and recently it was shown that mitochondrial ROS are the direct cause of increased concentrations of MG and thus AGEs formation in diabetic hyperglycemia (Nishikawa et al., 2000). Since TNF-induced cell death in L929 cells is characterized by increased production of mitochondrial ROS (Goossens et al., 1995; Goossens et al., 1999) which are essential for cell death and increased levels of MG, we tested whether irreversible protein modification by MG plays a role in TNF-induced cell death. For this we used aminoguanidine, a nucleophilic hydrazine compound and inhibitor of advanced nonenzymatic glycosylation product formation (Brownlee et al., 1986). The percentage of cell death in L929 cells after 16 hours of TNF treatment (20 U/ml) with and without aminoguanidine is shown in FIG. 5. A maximum inhibition of cell death of 25% was obtained in the presence of 600 or 800 µM of aminoguanidine and 15% inhibition in the presence of 400 µM. This inhibition was less pronounced (average of 15% to 20%) when the cells died more rapidly by giving higher doses of TNF (500–1000 U/ml). This could be due to the fact that the reaction of aminoguanidine with MG and MG-modified proteins is rather slow and that the MG protein modifications that occur during TNF-induced cell death are more rapid at higher doses of TNF and could even be enzymatically catalyzed. These data indicate that irreversible protein modification by methylglyoxal might play a role in TNF-induced cell death.

Example 7

Figure 6:
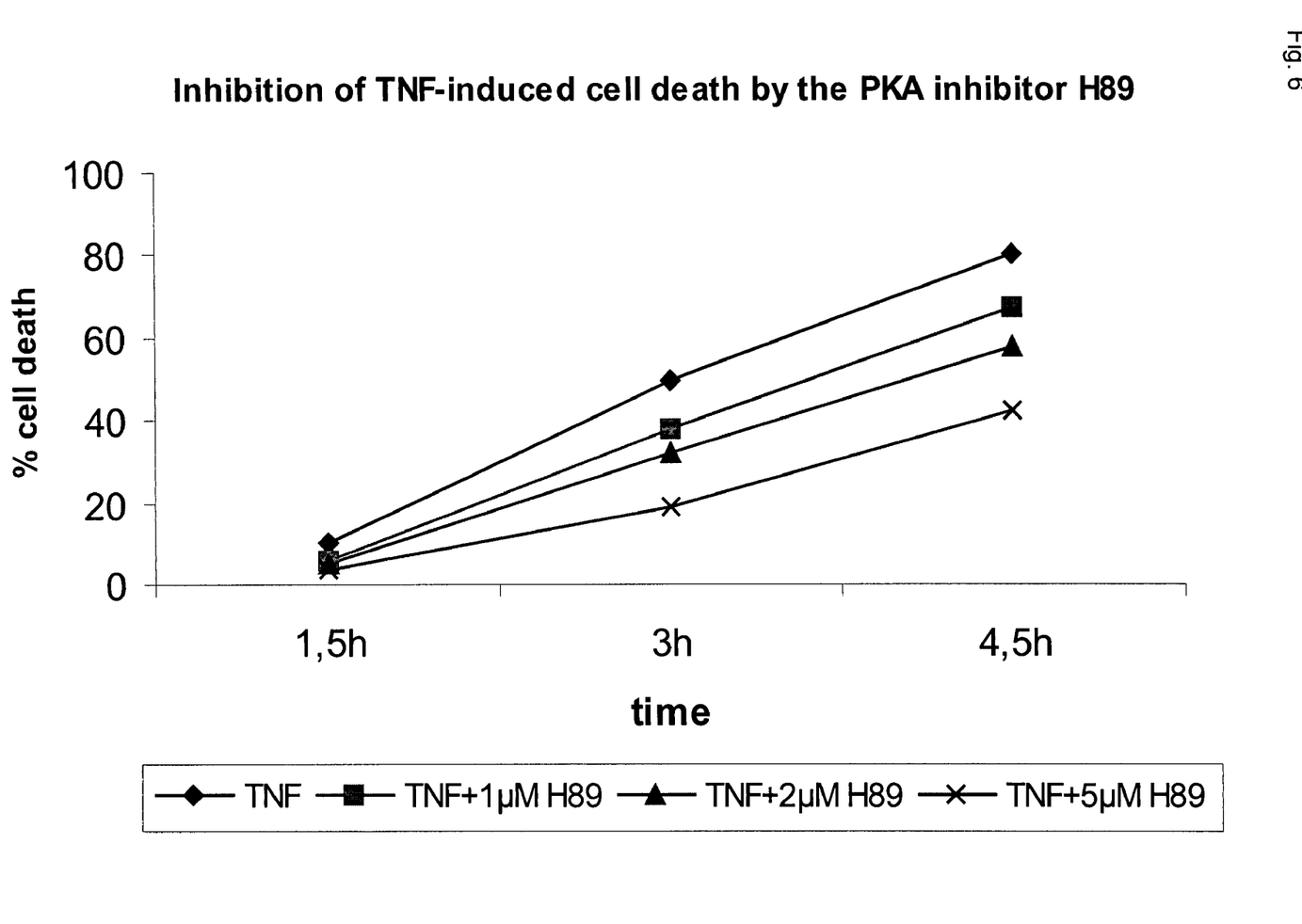
FIG. 6: inhibition of TNF-induced cell death by the PKA inhibitor H89, in function of the incubation time. The concentration of the inhibitor H89 is as indicated on the graph.
Figure 7:
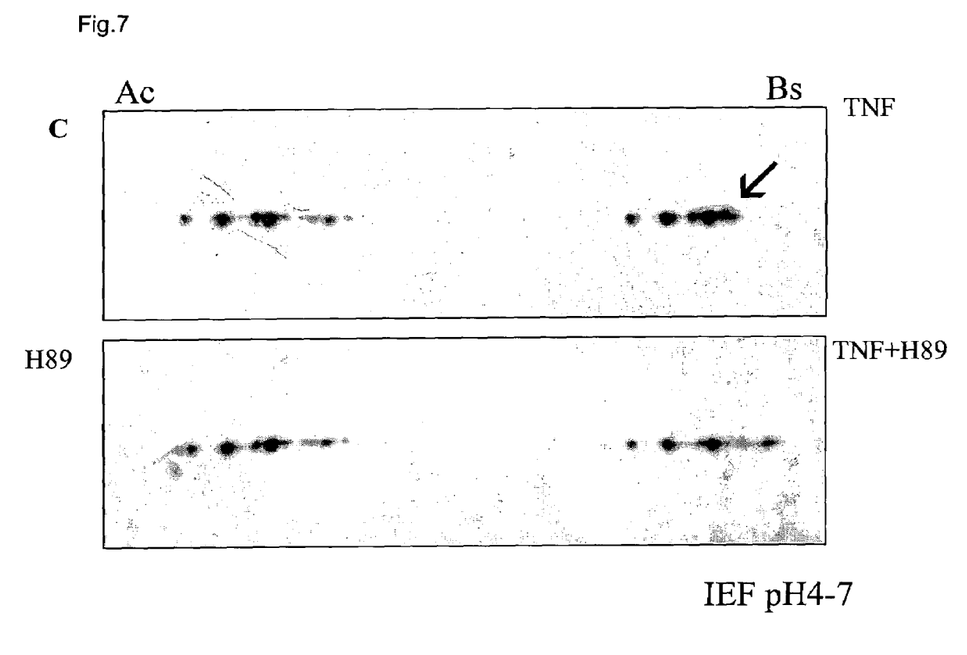
FIG. 7: western blot of a 2-dimensional gel (IEF pH 4–7) developed with a polyclonal antibody against human GLO1. C: control; TNF: TNF-treated sample; H89: control sample with addition of the PKA inhibitor H89; TNF+H89: TNF-treated sample, with addition of the PKA inhibitor H89. Ac and Bs indicate the acidic (Ac) and basic (Bs) side of the gel. Upon TNF treatment of the cells, a more acidic isoform of GLO1 becomes apparent; the arrow indicates the more acidic phosphorylated form. This new isoform is derived from the most basic isoform, present in the control cells, and its formation is inhibited by the presence of the PKA inhibitor H89. Note that the two-dimensional pattern of the TNF-treated sample in the presence of H89 is identical to the control sample C and the control sample H89.

The PKA Inhibitor Inhibits TNF-induced Cell Death and TNF-induced Phosphorylation of Glyoxalase I As it has already been shown that PKA is activated by TNF (Zhang et al., 1988), we examined whether pretreatment (2 hours) of L929 cells with the PKA inhibitor H89 had an effect on TNF-induced cell death. As shown in FIG. 6, the PKA inhibitor inhibits TNF-induced cell death in a concentration-dependent fashion and to a similar extent as the glyoxalse I inhibitor. Even an inhibitory effect was already obtained at relatively low concentrations of the inhibitor (1 μM), while at the highest concentration (5 μM) an inhibition of more then 50% was obtained. These data thus indicate that PKA plays a role in TNF-induced cell death. Next, we examined whether PKA was also responsible for the TNF-induced phosphorylation of endogeneous glyoxalase I in L929 cells. As shown in FIG. 3 and FIG. 7, pretreatment of the cells with the PKA inhibitor (5 μM) completely abolished the induction of the more acidic isoform by TNF. This suggests that the inhibitory effect of the PKA inhibitor on TNF-induced cell death could be largely due to the inhibition of phosphorylation of glyoxalase I.

Example 8

Formation of a Specific Methylglyoxal-derived AGE During TNF-induced Cell Death

Given the demonstrated role of MG in AGE formation and the accumulation of MG noted in response to TNF treatment, we next sought to determine whether irreversible protein modification by MG is a critical step in TNF-induced cell death. Immunoblots of L929 protein extracts were performed with a monoclonal antibody raised against in vitro MG-modified keyhole limpet hemocyanin. This antibody (mAb6B) recognizes epitopes in arterial walls of diabetic kidneys and of tissue injured by ischemia/reperfusion (Oya et al., 1999). The immunoblots showed a distinct differential protein band specifically present in TNF-treated (2.5 hours) cells along with several protein bands that were present in both the control and TNF-treated cells (FIG. 2A). The band was already present, although very weakly, after 1.5 hours of TNF treatment. These data indicate that protein modification by MG is not a random process during TNF-induced cell death, but rather involves specific target molecules for MG.

Figure 8A:
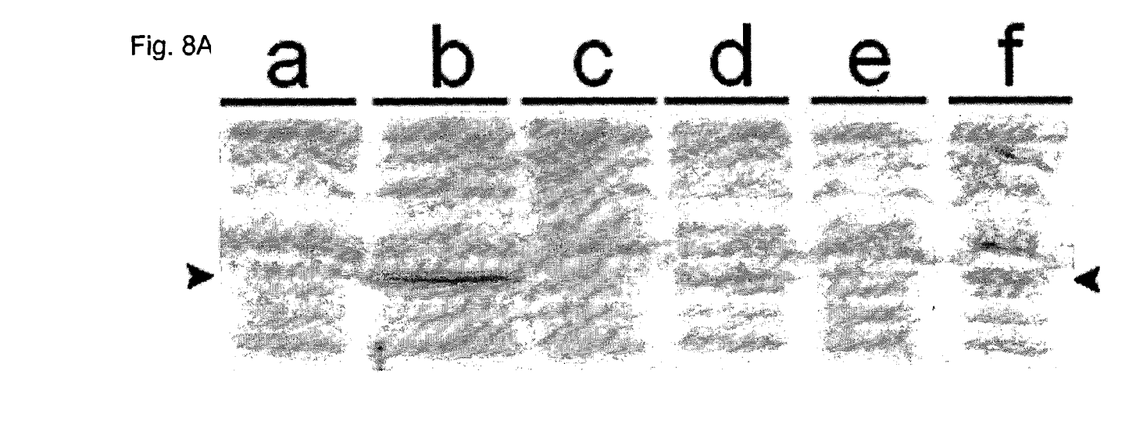
FIG. 8: Formation of a specific MG-derived AGE during TNF-induced cell death and the inhibition by several agents.
Figure 9:
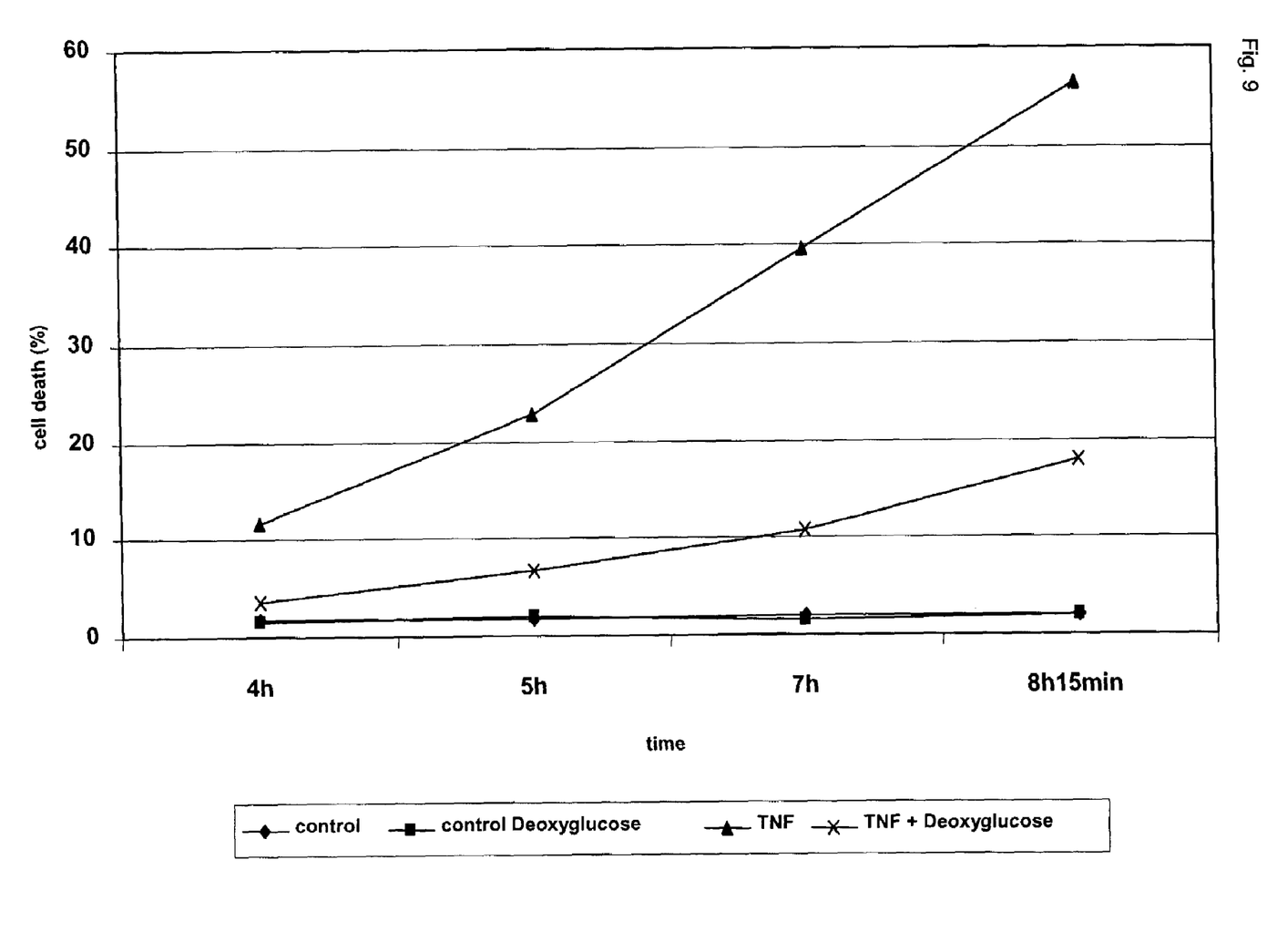
FIG. 9: The anti-glucose metabolite 2-deoxyglucose strongly inhibits TNF-induced cell death in L929 cells. TNF-induced cell death was measured as a function of time by flow cytometry using propidium iodide (PI) uptake as parameter for the percentage of death cells. 2-Deoxyglucose was used in a 2:1 ratio to glucose.

To demonstrate that the TNF-induced MG-derived AGE identified here by the antibody was formed as a consequence of oxidative stress, as in the case of diabetic hyperglycemia (Nishikawa et al., 2000), and only under cytotoxic conditions, L929 cells were treated with the anti-oxidant BHA. BHA arrests TNF-induced ROS production and cell death (Goossens et al., 1995). The formation of this specific MG-derived AGE in TNF-treated cells, as measured by densitometric analysis of the ECL signal from immunoblots, was reduced by 65% in the presence of BHA (FIG. 8A). The anti-glucose metabolite 2-deoxyglucose was then used to determine whether the TNF-induced increase in MG concentration was derived from glycolytic intermediates, which are usually considered to be the main intracellular source of MG. In the presence of 2-deoxyglucose (2:1 ratio to glucose), TNF-induced cell death was inhibited by 65% (FIG. 9), as was the formation of the specific MG-derived AGE noted in FIG. 8A. The possibility exists that inhibition of AGE formation in the presence of 2-deoxyglucose is an indirect result of the inhibition of mitochondrial ROS, which would mean the latter are derived from increased glycolysis. Indeed, it has been reported that TNF highly increases glycolysis and glucose uptake in L929 cells (Matthews, 1983; Kim and Kim, 2001).

Taken together, our results clearly indicate that glycolysis plays an important role in TNF-induced necrosis and that TNF-induced mitochondrial ROS, as in diabetic hyperglycemia, can lead to accumulation of MG and subsequent formation of a specific MG-derived AGE.

Example 9

Figure 8B:
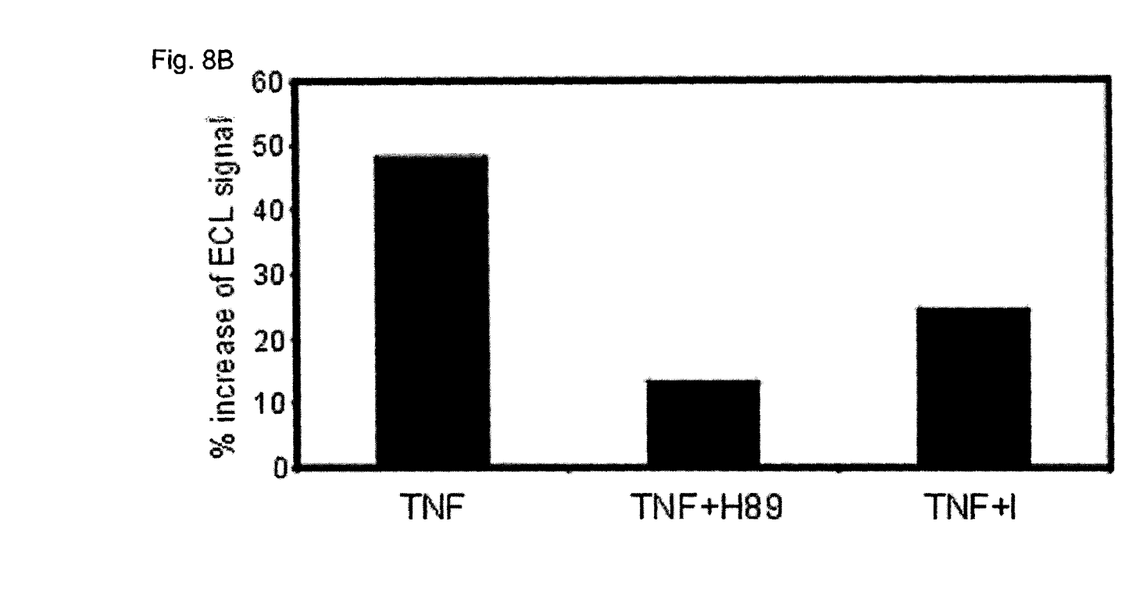
FIG. 8B: Formation of the specific MG-derived AGE is inhibited by the inhibitors that also inhibit the phosphorylation of GLO1. This figure represents the percentage relative increase of the ECL signal (as evaluated by scanning densitometry) of this specific MG-derived AGE in TNF-treated cells (1000 U/ml in the presence of CHX, 1.5 hours) over the background in control cells.

The TNF-induced Phosphorylation of GLO1 is Involved in Formation of the Specific MG-derived AGE Until now, AGE formation has been described as nonenzymatic, irreversible modifications of Lys and Arg residues slowly formed through long-term exposure to high concentrations of sugars and reactive compounds such as MG. Yet in TNF-induced cell death, MG-modification of proteins occurs very rapidly (within 1.5 to 2.5 hours of initiating TNF treatment). This suggests that MG-modification of specific target molecules could be enzymatically catalyzed by phosphorylated GLO1. To test this hypothesis, L929 cells were pretreated with s-p-bromobenzylglutathione cyclopentyl diester (BBGD 20 μM; kindly provided by Dr. P. Thomalley) and the PKA inhibitor H89 (5 μM), respectively, to determine whether these inhibitors of GLO1 phosphorylation interfere with the formation of MG-derived protein modifications during TNF-induced cell death. In cell cultures pretreated with BBGD and the PKA inhibitor, the formation of the specific MG-derived AGE, which is recognized by mAb6B, as measured by densitometric analysis of the ECL signal from immunoblots, was reduced by 50% and 70%, respectively, after 1.5 hours of TNF treatment (FIG. 8B). Inhibition was less pronounced (10% and 20% respectively) after 2.5 hours of TNF treatment, which could be due to the fact that, at later time points of TNF treatment, MG accumulation is dominant over the low basal levels of the phosphorylated form of GLO1 which are always present in L929 cells. The inhibitory effects with pretreatment of BBGD on TNF-mediated AGE formation and cell death is less pronounced during longer TNF treatments, possibly as a consequence of MG accumulation as described above. In any event, these data indicate that formation of the specific MG-derived AGE during cell death requires the TNF-induced phosphorylation of GLO1.

REFERENCES

Brownlee, M., H. Vlassara, A. Kooney, P. Ulrich and A. Cerami. (1986) Aminoguanidine prevents diabetes-induced arterial wall protein cross-linking. *Science* 232, 1629–1632.

Carswell, E. A., L. J. Old, R. L. Kassel, S. Green, N. Fiore and B. Williamson. (1975) An endotoxin-induced serum factor that causes necrosis of tumors. *Proc. Natl. Acad. Sci. U.S.A.* 72, 3666–3670.

Chaplen, F. W., W. E. Fahl and D. C. Cameron. (1998) Evidence of high levels of methylglyoxal in cultured Chinese hamster ovary cells. *Proc. Natl. Acad. Sci. U.S.A.* 95, 5533–5538.

Chaplen, F. W. R., W. E. Fahl and D. C. Cameron. (1996) Method for determination of free intracellular and extracellular methylglyoxal in animal cells grown in culture. *Anal. Biochem.* 238, 171–178.

Corman, B., M. Duriez, P. Poitevin, D. Heudes, P. Bruneval, A. Tedgui and B. I. Levy. (1998) Aminoguanidine prevents age-related arterial stiffening and cardiac hypertrophy. *Proc. Natl. Acad. Sci. U.S.A.* 95, 1301–1306.

Davidson, S. D., J. P. Cherry, M. S. Choudhury, H. Tazaki, C. Mallouh, C and S. Konno. (1999) Glyoxalase I activity in human prostate cancer: a potential marker and importance in chemotherapy. *J. Urol.* 161, 690–691.

De Vos, K., F. Severin, F. Van Herreweghe, K. Vancompernolle, V. Goossens, A. Hyman and J. Grooten. (2000)

Tumor necrosis factor induces hyperphosphorylation of kinesin light chain and inhibits kinesin-mediated transport of mitochondria. *J. Cell Biol.* 149, 1207–1214.

Fiers, W., R. Beyaert, W. Declercq and P. Vandenabeele. (1999) More than one way to die: apoptosis, necrosis and reactive oxygen damage. *Oncogene* 18, 7719–7730.

Gevaert, K., H. Demol, M. Puype, D. Broekaert, S. De Boeck, T. Houthaeve and J. Vandekerckhove. (1997) Peptides adsorbed on reverse-phase chromatographic beads as targets for femtomole sequencing by post-source decay matrix assisted laser desorption ionization-reflectron time of flight mass spectrometry (MALDI-RETOF-MS). *Electrophoresis* 18, 2950–2960.

Gevaert, K., H. Demol, T. Sklyarova, J. Vandekerckhove and T. Houthaeve. (1998) A peptide concentration and purification method for protein characterization in the subpicomole range using matrix assisted laser desorption/ionization-postsource decay (MALDI-PSD) sequencing. *Electrophoresis* 19, 909–917.

Goossens, V., K. De Vos, D. Vercammen, M. Steemans, K. Vancompernolle, W. Fiers, P. Vandenabeele and J. Grooten. (1999) Redox regulation of TNF signaling. *Biofactors* 10, 145–156.

Goossens, V., J. Grooten, K. De Vos and W. Fiers. (1995) Direct evidence for tumor necrosis factor-induced mitochondrial reactive oxygen intermediates and their involvement in cytotoxicity. *Proc. Natl. Acad. Sci. USA.* 92, 8115–8119.

Guy, G. R., X. Cao, S. P. Chua and Y. H. Tan. (1992) Okadaic acid mimics multiple changes in early protein phosphorylation and gene expression induced by tumor necrosis factor or interleukin-1. *J. Biol. Chem.* 267, 1846–1852.

Guy, G. R., S. P. Chua, N. S. Wong, S. B. Ng and Y. H. Tan. (1991). Interleukin 1 and tumor necrosis factor activate common multiple protein kinases in human fibroblasts. *J. Biol. Chem.* 266, 14343–14352.

Inoue, Y., B. Y. Choi, K. Murata and A. Kimura. (1990) Sexual response of *Saccharomyces cerevisiae*: phosphorylation of yeast glyoxalase I by a cell extract of mating factor-treated cells. *J. Biochem. (Tokyo)* 108, 4–6.

Jones, M. B., H. Krutzsch, H. Shu, Y. Zhao, L. A. Liotta, E. C. Kohn and E. F. Petricoin III. (2002) Proteomic analysis and identification of new biomarkers and therapeutic targets for invasive ovarian cancer. *Proteomics*. 2, 76–84.

Kalapos, M. P. (1999) On the promine/retine theory of cell division: now and then. *Biochem. Biophys. Acta* 1426, 1–16.

Kim, Y. H. and S. S. Kim. (2001) Bcl–2 in L929 cells inhibits tumor necrosis factor-mediated increase in glycolysis and accelerates tricarboxylic acid cycle. *Cancer Detection and Prevention*, 24 (Supplement 1).

Matthews, N. (1983) Anti-tumour cytotoxin produced by human monocytes: studies on its mode of action. *Br. J. Cancer* 48, 405–410.

McLellan, A. C., S. A. Phillips, P. J. Thornalley. (1992) Fluorometric assay of D-lactacte. *Anal. Biochem.* 206 (1), 12–16.

Nishikawa, T., D. Edelstein, X. L. Du, S. Yamagishi, T. Matsumura, Y. Kaneda, M. A. Yorek, D. Beebe, P. J. Oates, H. P. Hammes, I. Giardino and M. Brownlee. (2000) Normalizing mitochondrial superoxide production blocks three pathways of hyperglycaemic damage. *Nature* 404, 787–790.

Oya, T., N. Hattori, Y. Mizuno, S. Miyata, S. Maeda, T. Osawa and K. Uchida. (1999) Methylglyoxal modification of protein. Chemical and immunochemical characterization of methylglyoxal-arginine adducts. *J. Biol. Chem.* 274, 18492–18502.

Principato, G. B., V. Talesa, S. J. Norton, S. Contenti, C. Mangiabene and. G. Rosi. (1990) Induction of mouse liver glyoxalase I by hypobaric hypoxia. Biochem. Int. 20, 1019–1023.

Ranganathan, S., E. S. Walsh, A. K. Godwin and K. D. Tew. (1993) Cloning and characterization of human colon glyoxalase-I. *J. Biol. Chem.* 268, 5661–5667.

Rulli, A., L. Carli, R. Romani, T. Baroni, E. Giovannini, G. Rosi and V. Talesa. (2001) Expression of glyoxalase I and II in normal and breast cancer tissues. *Breast Cancer Res. Treat.* 66, 67–72.

Sakamoto, H., T. Mashima, A. Kizaki, S. Dan, Y. Hashimoto, M. Naito and T. Tsuruo. (2000) Glyoxalase I is involved in resistance of human leukemia cells to antitumor agent-induced apoptosis. *Blood* 95, 3214–3218.

Shamsi, F. A., E. Sharkey, D. Creighton and R. H. Nagaraj. (2000) Maillard reactions in lens proteins: methylglyoxal-mediated modifications in the rat lens. *Exp. Eye Res.* 70, 369–380.

Shinohara, M., P. J. Thornalley, I. Giardino, P. Beisswenger, S. R. Thorpe, J. Onorato and M. Brownlee. (1998) Overexpression of glyoxalase-I in bovine endothelial cells inhibits intracellular advanced glycation endproduct formation and prevents hyperglycemia-induced increases in macromolecular endocytosis. *J. Clin. Invest.* 101, 1142–1147.

Spengler, B., D. Kirsch, R. Kaufmann and E. Jaeger. (1992) Peptide sequencing by matrix-assisted laser-desorption mass spectrometry. *Rapid Commun. Mass Spectrom.* 6, 105–108.

Thornalley, P. J., L. G. Edwards, Y. Kang, C. Wyatt, N. Davies, M. J. Ladan and J. Double. (1996) Anti-tumour activity of S-p-bromobenzylglutathione cyclopentyl diester in vitro and in vivo. Inhibition of glyoxalase I and induction of apoptosis. *Biochem. Pharmacol.* 51, 1365–1372.

Vancompernolle, K., T. Boonefaes, M. Mann, W. Fiers and J. Grooten. (2000) Tumor necrosis factor-induced microtubule stabilization mediated by hyperphosphorylated oncoprotein 18 promotes cell death [In Process Citation]. *J. Biol. Chem.* 275, 33876–33882.

Vince, R. and W. B. Wadd. (1969) Glyoxalase inhibitors as potential anti-cancer agents. *Biochem. Biophys. Res. Commun.* 34, 593–598.

Wallach, D., E. E. Varfolomeev, N. L. Malinin, Y. V. Goltsev, A. V. Kovalenko and M. P. Boldin. (1999) Tumor necrosis factor receptor and Fas signaling mechanisms. *Annu. Rev. Immunol.* 17, 331–367.

Zhang, Y. H., J. X. Lin, Y. K. Yip and J. Vilcek. (1988) Enhancement of cAMP levels and of protein kinase activity by tumor necrosis factor and interleukin 1 in human fibroblasts: role in the induction of interleukin 6. *Proc. Natl. Acad. Sci. U.S.A.* 85, 6802–6805.

What is claimed is:

1. An isolated phosphorylated polypeptide consisting of the amino acid sequence of SEQ ID NO:1, phosphorylated at one or more positions selected from the group consisting of Ser 45 and Thr 98.

2. An isolated phosphorylated polypeptide comprising the amino acid sequence of SEQ ID NO: 1, phosphorylated at one or more positions selected from the group consisting of Ser 45 and Thr 98.

* * * * *

UNITED STATES PATENT AND TRADEMARK OFFICE
CERTIFICATE OF CORRECTION

| | |
|---|---|
| PATENT NO. | : 7,198,931 B2 |
| APPLICATION NO. | : 10/630451 |
| DATED | : April 3, 2007 |
| INVENTOR(S) | : Katia Vancompernolle |

It is certified that error appears in the above-identified patent and that said Letters Patent is hereby corrected as shown below:

| | | |
|---|---|---|
| COLUMN 12, | LINE 17, | change "Dr. P. Thomalley" to --Dr. P. Thornalley-- |
| COLUMN 13, | LINE 21, | change "Vancompemolle" to --Vancompernolle-- |
| COLUMN 13, | LINE 57, | change "P. J. Thomally." to --P. J. Thornally.-- |
| COLUMN 14, | LINE 28, | change "P. J. Thomally," to --P. J. Thornally,-- |

Signed and Sealed this

Seventh Day of July, 2009

JOHN DOLL
*Acting Director of the United States Patent and Trademark Office*